United States Patent [19]

Sawa et al.

[11] 3,932,384
[45] Jan. 13, 1976

[54] DIBENZAZECINES

[75] Inventors: Yoshiro Sawa, Ashiya; Katsumi Hirose, Nishinomiya; Shin Maeda; Yoshinori Hamada, both of Amagasaki, all of Japan

[73] Assignee: Shionogi & Co., Ltd., Osaka, Japan

[22] Filed: July 27, 1973

[21] Appl. No.: 383,148

[30] Foreign Application Priority Data

Aug. 17, 1972 Japan.............................. 47-82399
Aug. 17, 1972 Japan.............................. 47-82400
Sept. 26, 1972 Japan.............................. 47-96368

[52] U.S. Cl....... 260/239 D; 260/289 A; 260/340.3; 260/340.5; 424/244; 424/278; 424/282
[51] Int. Cl.²............... C07D 225/08; C07D 491/04
[58] Field of Search.................... 260/239 D

[56] References Cited
UNITED STATES PATENTS 3,498,988 3/1970 Houlihan et al................ 260/239 D

OTHER PUBLICATIONS

Casadio et al., J. Med. Chem., Vol. 13, pp. 1092–1095 (1970). RSIJ5

*Primary Examiner*—Alton D. Rollins
*Attorney, Agent, or Firm*—Wenderoth, Lind & Ponack

[57] ABSTRACT

Dibenzazecines of the general formula:

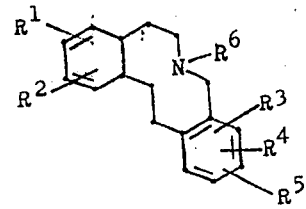

(wherein $R^1$ and $R^2$ are the same or different, each representing a hydrogen atom, a hydroxy group, a lower alkoxy group, an aralkoxy group, or a hydroxymethyl group; or when adjacent to and taken together with each other, they can be an alkylenedioxy group; $R^3$, $R^4$, and $R^5$ are the same or different, each representing a hydrogen atom, a hydroxy group, or a lower alkoxy group, or two of them, when adjacent and bound to each other, they can be an alkylenedioxy group; and $R^6$ represents a hydrogen atom, an alkyl group, an alkenyl group, an aralkyl group or a cycloalkyl group) or acid addition salts thereof, exhibiting CNS depressant actions such as analgesic action, sedative action, and so on; which can be produced from the dibenzoquinolizines.

8 Claims, No Drawings

DIBENZAZECINES

This invention relates to a novel class of dibenzazecines and to processes for their production.

More particularly, this invention relates to therapeutically valuable 5,6,7,8,13,14-hexahydrodibenz[c,g]azecines represented by the general formula:

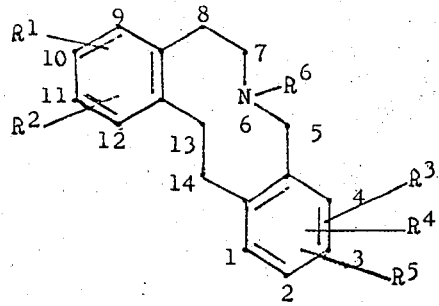

(I)

wherein $R^1$ and $R^2$ are the same or different, and each is a member selected from the group consisting of hydrogen atom, hydroxy group, lower alkoxy group, aralkoxy group and hydroxymethyl group; or when adjacent to and taken together with each other, they can be an alkylenedioxy group; $R^3$, $R^4$, and $R^5$ are the same or different, and each is a member selected from the group consisting of hydrogen atom, hydroxy group, and lower alkoxy group; or two of them, when adjacent and bound to each other, can be an alkylenedioxy group; and $R^6$ is a member selected from the group consisting of hydrogen atom, alkyl group, alkenyl group, aralkyl group, and cycloalkyl group. The following such cases are excluded from the above definition: all of $R^1$ to $R^5$ are hydrogen atoms concurrently; while $R^1$ and $R^2$, taken together with each other, form a 10,11-methylenedioxy group and two of $R^3$, $R^4$, and $R^5$ are 3- and 4-methoxy groups, the remaining of $R^3$, $R^4$ and $R^5$ is a hydrogen atom and $R^6$ is a methyl group; and while $R^1$ and $R^2$ are 10- and 11-methoxy groups and two of $R^3$, $R^4$, and $R^5$, taken together with each other, represent a 3,4-methylenedioxy group, the remaining of $R^3$, $R^4$ and $R^5$ is a hydrogen atom and $R^6$ is a methyl group.

The object of this invention is to provide the therapeutically valuable compounds of the above-mentioned general formula (I) exhibiting potent central nervous system depressant actions such as analgesic action, sedative action, and the like. Another object of this invention is to provide a processs for the production of such valuable compounds (I).

The starting compounds used in this invention can be shown by the general formula (II) and derived from naturally occurring dibenzoquinolizine alkaloids such as berberine alkaloids (e.g., berberine, lambertine, berlambine), or can be produced by means of total syntheses.

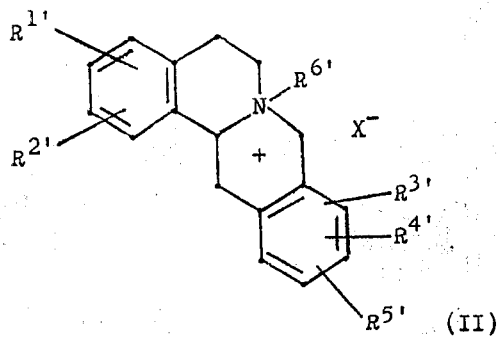

(II)

wherein $R^{1'}$ and $R^{2'}$ are the same or different, and each is a member selected from the group consisting of hydrogen atom, hydroxy group, lower alkoxy group, aralkoxy group, and hydroxymethyl group; or when adjacent to and taken together with each other, they can be an alkylenedioxy group; $R^{3'}$, $R^{4'}$, and $R^{5'}$ are the same or different, and each is a member selected from the group consisting of hydrogen atom, hydroxy group, and lower alkoxy group; or two of them, when adjacent and bound to each other, can be an alkylenedioxy group; $R^{6'}$ is a member selected from the group consisting of alkyl group, alkenyl group, aralkyl group, and cycloalkyl group; and X is a halogen atom. Special case of all of $R^{1'}$ to $R^{5'}$ being hydrogen atoms is excluded from this definition.

In the above definition, the lower alkoxy group means those of up to 6 carbon atoms such as methoxy, ethoxy, n-propoxy, isopropoxy, n-butoxy, isobutoxy, t-butoxy, n-pentyloxy, n-hexyloxy, and the like. The aralkoxy group means those of 7 to 9 carbon atoms such as benzyloxy, phenethyloxy, p-methylbenzyloxy, and the like. The alkylenedioxy group means methylenedioxy group, ethylenedioxy group, trimethylenedioxy group, and the like. The alkyl group means those of up to 6 carbon atoms such as methyl, ethyl, n-propyl, isopropyl, n-butyl, isobutyl, s-butyl, t-butyl, n-pentyl, n-hexyl, and the like. The alkenyl group means those of 3 to 6 carbon atoms such as allyl, 2-butenyl, 3-methyl-2-butenyl, and the like. The aralkyl group means those of 7 to 9 carbon atoms such as benzyl, phenethyl, p-methylbenzyl, p-methoxybenzyl, and the like. The cycloalkyl group means those of up to 7 carbon atoms such as cyclopropyl, cyclopropylmethyl, cyclobutylmethyl, cyclopentyl, cyclohexyl, cyclohexylmethyl, and the like. The halogen atom means chlorine, bromine and iodine.

According to the present invention, the objective compounds (I), excepting the case of $R^6 = H$, can be produced from the dibenzoquinolizinium halides of the general formula (II) by means of the Hofmann degradation followed by reduction of the intermediate 13,14-unsaturated or of dissolving metal reduction. The compounds (I) in which $R^6$ is a hydrogen atom can be produced from the corresponding materials (I) in which $R^6$ is a benzyl group or an alkyl or aralkyl group, by reductive elimination of the benzyl group or oxidation of the alkyl or aralkyl group followed by acid or basic hydrolysis. In addition, the compounds (I), excepting the case of $R^6 = H$, can also be produced from the starting materials (I), in which $R^6$ is a hydrogen atom, by the N-substitution or the formation of the Schiff bases of amides followed by reduction.

The conversion of the starting dibenzoquinolizinium halides (II) to the objective dibenzazecines (I) ($R^6 \neq H$) is due to the rupture of the C-N linkage by the Hofmann degradation or by dissolving metal reduction (reduction by metal - liquid ammonia).

In the process through the Hofmann degradation, the starting compounds (II) afford their intermediates, 13,14-dehydro derivatives of the general formula (III), as the degradation product,

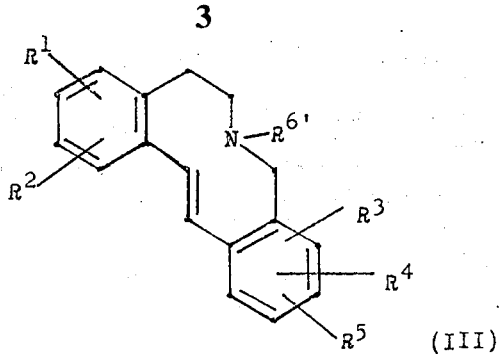

(wherein $R^1$, $R^2$, $R^3$, $R^4$, and $R^5$ each has the same meaning as mentioned bbove, $R^{6'}$ has the same meaning as $R^6$ does but must be not a hydrogen atom) which are reduced to the objective compounds (I) by means of catalytic hydrogenation or dissolving metal reduction.

The Hofmann degradation of the compounds (II) may be carried out in a conventional manner. For example, the halide ion ($X^-$) of the compounds (II) is displaced by the hydroxide ion ($OH^-$), and the resulting quaternary ammonium hydroxide is permitted to the degradation to yield the intermediate (III). The displacement of the halide ion by the hydroxide ion is usually effected by treatment of the halides (II) with silver oxide in a polar solvent such as methanol, ethanol, propanol, ethylene glycol, propylene glycol, and the like, at an elevated temperature such as reflux temperature of the solvent used. The subsequent degradation is effected by heating the quaternary ammonium hydroxide in or without a solvent as mentioned above. Particularly, in the present invention, it is very preferable to effect the degradation in dimethylsulfoxide at room temperature.

Alternatively, the rupture of the C-N linkage of the starting compounds (II) may also be effected on treatment with a base such as alkoxides (e.g., sodium ethoxide, potassium tertbutoxide), phenoxides (e.g., sodium phenoxide), or carbonates (e.g., potassium carbonate, sodium carbonate); or with an ion exchange resin.

The resulting 13,14-dehydro intermediate (III) is reduced by means of catalytic hydrogenation or dissolving metal reduction.

The catalytic hydrogenation of the 13,14-dehydro derivatives (III) may be effected in a conventional manner using metal catalysts such as platinum catalysts, palladium catalysts, nickel catalysts, rhodium catalysts, and the like. The hydrogenation is usually conducted at room temperature in a suitable solvent such as alcohols (e.g., methanol, ethanol), ethers (e.g., diethyl ether, tetrahydrofuran, dimethoxyethane), esters (e.g., ethyl acetate), acids (e.g., acetic acid), and water.

The dissolving metal reduction of the 13,14-dehydro derivatives (III) may be effected by an alkali metal or alkaline earth metal in liquid ammonia. The reaction may be carried out substantially in the same manner as in the rupture of the C-N linkage by metal - liquid ammonia reduction as mentioned below.

An alternative process for the rupture of the C-N linkage is the dissolving metal reduction (metal - liquid ammonia reduction). The reaction is usually carried out under cooling at a temperature below the boiling point of ammonia (−33°C) in the presence of an alkali metal (e.g., lithium, sodium, potassium) or an alkaline earth metal (e.g., calcium, barium) in liquid ammonia. The reaction may also carried out in a tightly closed vessel (e.g., autoclave) at a temperature over the boiling point of ammonia, for example, at room temperature or under heating. In general, the reaction mixture turns dark blue, and this color disappears as the reaction proceeds. In this stage, an additional amount of the metal is added to the reaction mixture in small portions, and the termination of the reaction may be determined by the continuous coloration. In carrying out the reaction, it is appropriate to use an aprotic solvent as co-solvent such as diethyl ether, tetrahydrofuran, dioxane, 1,2-dimethoxyethane, and the like. Additionally, an alcohol (e.g., ethanol, isopropanol, tertbutanol) or carboxylic acid (e.g., acetic acid) may be used as a proton source. In place of ammonia, an aliphatic amine such as methylamine, ethylamine, and the like may be used; the reaction may be carried out practically in the same manner as in the case of liquid ammonia.

In this metal - ammonia reduction, when $R^{1'}$ and $R^{2'}$, and/or two of $R^{3'}$, $R^{4'}$, and $R^5$ hold a methylenedioxy group, such a group may also ruptured to yield the hydroxy derivatives as illustrated below by the partial formulae.

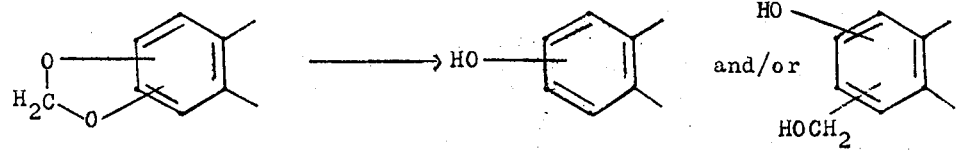

The objective compounds (I), in which $R^6$ is a hydrogen atom, can be produced on the removal of the N-substituents from the compounds (I) prepared in a similar manner as described above in which $R^6$ is a benzyl group, or an alkyl or aralkyl group.

The removal of the N-benzyl group can be achieved by reductive elimination (hydrogenolysis) as illustrated below:

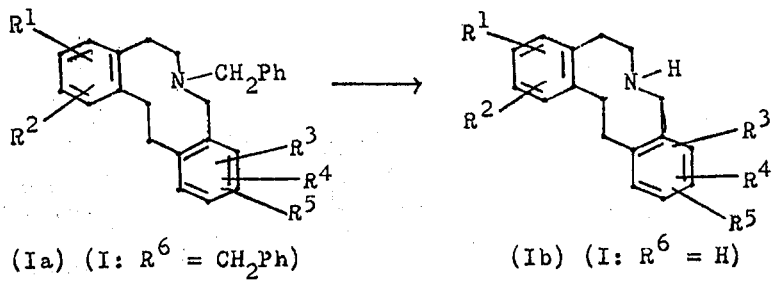

(Ia) (I: $R^6 = CH_2Ph$)   (Ib) (I: $R^6 = H$)

(wherein $R^1$, $R^2$, $R^3$, $R^4$, and $R^5$ each has the same meaning as mentioned above).

The hydrogenolysis of the N-benzyl derivative (Ia) may be effected by means of catalytic hydrogenation using a metal catalyst. The reaction is carried out in a conventional manner, for example, in a suitable solvent such as alcohols (e.g., methanol, ethanol), ethers (e.g., tetrahydrofuran, dimethoxyethane), esters (e.g., ethyl acetate), and the like, in hydrogen atmosphere at room temperature or under heating with shaking or stirring. The preferred catalyst used in this reaction is platinum catalyst (e.g., platinum oxide, platinum black), palladium catalyst (e.g., palladium black, palladium carbon, palladium on alumina, palladium on barium sulfate, palladium on calcium carbonate), or nickel catalyst (e.g., Raney nickel, Urushibara nickel). The hydrogenolysis usually proceeds well under usual pressure (atmospheric pressure), and if required, it is also possible to carry out the reaction under increased pressure or in the presence of a small amount of an acid as a reaction-accelerating agent such as acetic acid, hydrochloric acid, perchloric acid, and the like.

The removal of the N-alkyl or aralkyl group can be effected by oxidation of the N-alkyl or aralkyl group with a suitable oxidizing agent, and subsequent acid or basic hydrolysis, as illustrated below:

using an inorganic acid such as hydrochloric acid, hydrobromic acid, sulfuric acid, and the like; or an organic acid such as formic acid, acetic acid, trifluoroacetic acid, p-toluenesulfonic acid, and the like, at room temperature or under heating, if required in a suitable solvent such as water, methanol, ethanol, tert-butanol, tetrahydrofuran, dioxane, dimethylsulfoxide, dimethylformamide, and the like.

The resulting N-free derivatives (Ib), if required, can be converted into the corresponding N-substituted compounds (Ic) (I: $R^6$ = H) by the N-substitution, the formation of the Schiff bases, or amides followed by reduction.

The N-substitution can be effected in a usual manner used in the introduction of alkyl groups, alkenyl groups, aralkyl groups, or cycloalkyl groups into amino groups; that is, practically accomplished by means of a reagent for introducing such groups into amino groups. Examples of such reagents are so-called alkylating agents such as corresponding halogenides of the substituents $R^{6'}$ (e.g., methyl iodide, ethyl bromide, allyl bromide, 3-methyl-2-butenyl bromide, benzyl bromide, cyclopropylmethyl bromide, cyclohexylmethyl iodide), sulfates (e.g., dimethyl sulfate, diethyl sulfate), sulfonates (e.g., methyl methanesulfonate, ethyl trifluoromethanesulfonate, propyl p-toluenesulfonate), and the

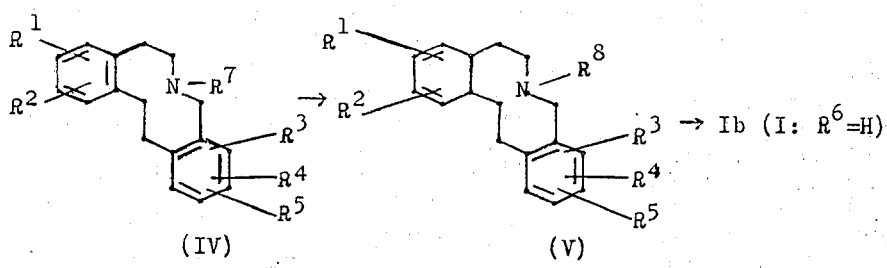

(wherein $R^1$, $R^2$, $R^3$, $R^4$, and $R^5$ each has the same meaning as described above; $R^7$ is an alkyl group or an aralkyl group; and $R^8$ is an acyl group or a formyl group).

The oxidation of the compounds (IV) is effected by means of an oxidizing agent, particularly suitable in this reaction, chromic acid - pyridine complex. In the said reaction the methylene group adjacent to the nitrogen atom is oxidized to the carbonyl group, for example, when $R^7$ is a methyl group, the oxidation affords the compounds (V) in which $R^8$ is a formyl group; and when $R^7$ is a benzyl group, $R^8$ is a benzoyl group. Accordingly, at least the adjacent position ($\alpha$-carbon atom) of the nitrogen atom in the substituent $R^7$ has to be the methylene group in the starting compounds (IV). The oxidation is usually carried out at room temperature or under cooling.

The subsequent hydrolysis is effected on treatment with an acid or base in a conventional manner. In general, the hydrolysis is carried out in an acid condition like. The reaction is usually carried out at room temperature or under heating in the presence of a suitable acid-abstracting agent such as inorganic bases or organic bases, for example, alkali metal carbonates (e.g., sodium carbonate, potassium carbonate), alkali metal bicarbonates (e.g., sodium bicarbonate, potassium bicarbonate), alkali metal hydroxides (e.g., sodium hydroxide, potassium hydroxide), triethylamine, pyridine, and the like. In this reaction, it is also appropriate to use a solvent such as alcohols (e.g., methanol, ethanol, tert-butanol, 2-ethoxyethanol), ethers (e.g., tetrahydrofuran, dioxane, dimethoxyethane), halogeno-hydrocarbons (e.g., methylene chloride, chloroform, dichloroethane), dimethylformamide, dimethylsulfoxide, and the like.

Alternatively, the N-substitution can also be achieved by the Schiff base formation or amide formation, and subsequent reduction of the C=N unsaturation of the Schiff base or of the C=O group of the amide formed. The reaction sequence can be illustrated as follows:

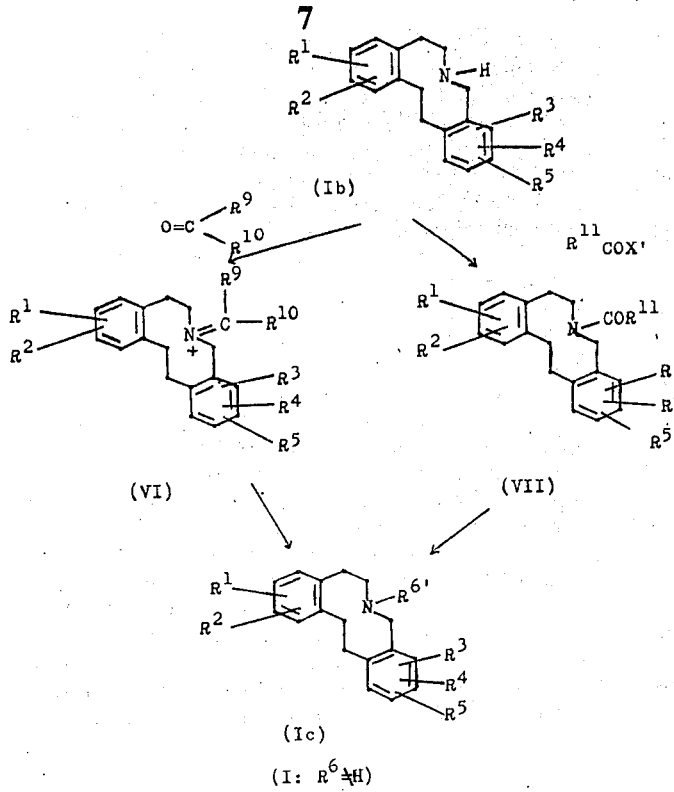

(wherein $R^1$, $R^2$, $R^3$, $R^4$, $R^5$, and $R^{6'}$ each has the same meaning as described above; $R^9$-C-$R^{10}$ and $COR^{11}$ mean those which can be converted into the substituent $R^{6'}$ by the reduction; and X' is a halogen atom or a hydrocarbonoxy group)

The formation of the Schiff bases (VI) from the N-free derivatives (Ib) can be accomplished by reaction with a carbonyl compound represented by the general formula $R^9$-CO-$R^{10}$. The carbonyl compound involves an aldehyde such as formaldehyde, acetaldehyde, propionaldehyde, isobutyraldehyde, benzaldehyde, and the like; and a ketone such as acetone, methyl ethyl ketone, and the like; which corresponds to the objective substituent $R^{6'}$. The reaction may be carried out in a conventional manner usually applied to the reaction for the Schiff base formation, for example, by treating the N-free derivatives (I) with the carbonyl compounds ($R^9$-CO-$R^{10}$) in a suitable solvent at room temperature or under heating. The subsequent reduction of the Schiff bases (VI) can be effected by means of catalytic hydrogenation or by a reducing agent.

The catalytic hydrogenation may be carried out in a conventional manner, for example, by shaking or stirring a mixture of the Schiff base (VI) and a catalyst (e.g., platinum catalyst, palladium catalyst, nickel catalyst) in hydrogen atmosphere at room temperature in a suitable solvent (e.g., methanol, ethanol, tetrahydrofuran, ethyl acetate). If required, the reaction may be conducted at an elevated temperature under increased pressure.

The reduction with a reducing agent can also be applied to this process. The preferred reducing agents are metal hydrides (e.g., lithium aluminum hydride, sodium borohydride, potassium borohydride) and formic acid (as seen in Leuckart-Wallach reaction). The reaction may be carried out in a conventional manner using such reducing agent, for example, in or without a suitable solvent such as methanol ethanol, ether, tetrahydrofuran, and the like, at room temperature or under heating.

It is particularly noteworthy that in this process the conversion of the N-free derivatives (Ib) to the N-substituted derivatives (Ic) (I : $R^6 \neq H$) can be accomplished in one step by carrying out the Schiff base formation in the aforementioned reduction condition.

An alternative route, the amide formation and subsequent reduction may be effected as follows. The amide formation (N-acylation) is accomplished by means of a reactive derivative ($R^{11}COX'$) of the carboxylic acid corresponding to the substituent $R^{6'}$ to be introduced. The reactive reagent of the carboxylic acid ($R^{11}COX'$) involves acid halides such as ethyl chloroformate, acetyl chloride, propionyl chloride, benzoyl chloride, etc., and the corresponding esters such as p-nitrophenyl esters. The said reaction may be carried out in a suitable solvent such as benzene, toluene, tetrahydrofuran, dioxane, pyridine, dimethylformamide, and the like, if required, in the presence of a base such as triethylamine, pyridine, potassium carbonate, and the like, at room temperature or under heating. The subsequent reduction may be carried out by means of a suitable reducing agent, for example, lithium aluminum hydride, sodium bis(methoxyethoxy)aluminum hydride, etc., in a solvent such as diethyl ether, tetrahydrofuran, benzene, toluene, and the like, at room temperature or reflux temperatures of the solvent used.

Additionally, it is also possible to directly introduce the substituent $R^{6'}$ under action of diazoalkane such as diazomethane, diazoethane, and the like, or by addition of unsaturated compound such as ethylene, propylene, and the like.

The aforementioned process for introducing the N-substituents $R^6$ is shown by certain examples of the heretofore known and frequently utilized processes for the N-substitution which can be applied to the present invention. Other traditional processes for the N-substitution not exemplified in this specification may also be applied to the present invention.

In some cases, the N-substitution is accompanied by ether formation on the phenolic hydroxy group when one or more of the substituents, $R^1$ to $R^5$ are free hydroxy radicals. Such side reactions are also included in the present invention.

Thus resulting N-substituted dibenzazecines (I), if required, are able to be converted into the corresponding acid addition salts on treatment with an organic or inorganic acid such as hydrochloric acid, hydrobromic acid, nitric acid, phosphoric acid, sulfuric acid, perchloric acid, acetic acid, propionic acid, oxalic acid, malonic acid, succinic acid, adipic acid, maleic acid, tartaric acid, lactic acid, citric acid, benzoic acid, salicyclic acid, methylsulfonic acid, ethanedisulfonic acid, sulfamic acid, and the like.

Table I indicates the analgesic activity and the acute toxicity of the representative compounds (I) prepared in the present invention.

cially available analgesic, aminopyrine. Moreover, they exhibit a remarkable sedative action.

When the compounds (I) prepared in this invention are employed as analgesic agents, they may be administered alone or in combination with pharmaceutically acceptable carriers, the proportion of which is determined by the solubility and chemical property of the compound, chosen route of administration, and standard pharmaceutical practice. For example, they may be injected parenterally in human adults, that is intramuscularly, intravenously or subcutaneously, at a dose of 25 to 300 mg in the form of a sterile aqueous solution containing 0.1 to 2 % of the active ingredient in a solute such as saline or glucose to make the solution isotonic. They may also be formulated with suitable excipients in the form of tablets or capsules for oral administration and can be administered in single or divided doses containing 100 to 1500 mg of the active ingredient.

Table I

| Compound No. | $R^1$ | $R^2$ | $R^3$ | $R^4$ | $R^5$ | $R^6$ | Salt | Analgesic action (mg/kg) Writhing | Haffner | Acute toxicity (mg/kg) |
|---|---|---|---|---|---|---|---|---|---|---|
| 1 | H | 11—OH | 4—OH | 3—OH | H | $CH_3$ | HBr | 26 | — | 50–100 |
| 2 | H | 11—OH | 4—$OCH_3$ | 3—$OCH_3$ | H | $CH_3$ | HCl | 23.2 | 58 | 54.9 |
| 3 | 10—OH | H | 4—$OCH_3$ | 3—$OCH_3$ | H | $CH_3$ | HCl | 22.3 | 37.9 | 231.4 |
| 4 | 10—$CH_2OH$ | 11—OH | 4—$OCH_3$ | 3—$OCH_3$ | H | $CH_3$ | — | 45 | — | >500 |
| 5 | H | 11—OH | 4—OH | H | H | $CH_3$ | $HClO_4$ | 50 | — | 300 |
| 6 | 10—OH | H | 4—OH | 3—OH | H | $CH_3$ | HBr | 75 | — | 300 |
| 7 | 10—OH | H | 4—$OCH_3$ | 3—$OCH_3$ | H | H | HCl | 26.5 | 250 | 500 |
| 8 | 10—OH | H | 4—$OCH_3$ | 3—$OCH_3$ | H | $-CH_2-\triangleleft$ | HCl | 80 | — | >1000 |
| Standard Aminopyrine | | | | | | | | 44 | 138 | 335 |

Test Method:

1. Analgesic activity (Writhing method);

DS-mice (15 to 17 g body weight, male and female) are treated with an intraperitoneal injection of 0.2 mg/10 g of 0.02 % phenylquinone solution as a writhing inducer and kept in an individual observation cage for 15 minutes after the administration of phenylquinone. In the control mice, the writhing syndrome occurs about 10 times during this period of time. When the mice treated with a test compound do not show this syndrome for a period of 15 minutes, the test compound can be estimated to have an analgesic activity. The $ED_{50}$ is calculated by the up-and-down method of Brownlee et al. [Fed. Proc., 18, 412 (1959)]

2. Analgesic activity (Haffner method);

The tail-roots of DS-mice (15 to 17 g body weight, male and female) are pinched with a pair of forceps. Pain responses, such as biting, head turning and vocalization are observed. All of the control animals respond to the noxious stimulus with in a period of one second. When the mice treated with a test compound do not show any withdrawal response within a period of 3 seconds, the test compound can be estimated to have an analgesic activity. The $ED_{50}$ is calculated by the Bliss' method [Ann. Appl. Biol., 22, 134; 307 (1935); Quat. J. Pharmacol., 11, 192 (1938)].

3. Acute toxicity

Ten DS-mice (15 to 17 g body weight, male and female) in every group are used in the test at each dose level. Each assay compound is tested in 4 to 5 doses. The mortality is counted during a period of 72 hours after the administration of the test compound. The $LD_{50}$ is calculated by the Bliss' method.

As indicated in Table I, a series of the dibenzazecines (I) prepared in the present invention show a potent analgesic action not less better than that of a commer- The invention will be better explained by the following examples which are not intended as a limitation thereof.

EXAMPLE 1

To a solution of 20.4 g of 7-benzyl-9,10-dimethoxy-2,3-methylenedioxy-5,6,7,8,13,13a-hexahydrodibenzo[a,g]quinolizinium bromide in 200 ml of methanol is added silver oxide freshly prepared from 13.6 g of silver nitrate, and the mixture is refluxed for 20 minutes under nitrogen atmosphere. After cooling, the mixture is filtered, and the filtrate is treated with 0.6 g of active carbon and evaporated to dryness under reduced pressure at a temperature below 40°C. The residue (18.75 g) is dissolved in 94 ml of dimethylsulfoxide and allowed to stand at room temperature for 15 minutes. Ice-water (40 ml) is added to the solution and the mixture is extracted with benzene. The extract is dried over anhydrous potassium carbonate, passed through a column of 100 g of alumina, and eluated with 250 ml of benzene to yield 13.69 g of a crude product, which on recrystallization from ether and then from acetone affords 7.49 g (43.6 %) of 6-benzyl-9,10-dimethoxy-2,3-methylenedioxy- 5,6,7,8-tetrahydrodibenz[c,g]azecine (the trans-isomer) as colorless crystals having mp. 129° – 132°C. UV: $\lambda_{max}^{EtOH}$ 288 m$\mu$ ($\epsilon$ 8039). NMR: $\delta$($CDCl_3$) 3.80 and 3.83 (each 3H, singlet, $OCH_3$), 3.53 and 3.97 (2H each, singlet, N-$CH_2$-Ar), 5.87 (2H, singlet, O-$CH_2$-O), 6.52 and 7.14 (1H each, doublet, J = 16.5, -CH=CH-). Anal. Calcd. for $C_{27}H_{27}NO_4$: C, 75.50%; H, 6.34%; N, 3.26%. Found: C, 75.64%; H, 6.41%; N, 3.36%.

The motor liquid of crystallization is evaporated to dryness, and the residue is dissolved in 27 ml of ethyl acetate, acidified with 2N-hydrochloric acid, and filtered to remove the precipitated by-products: 3-(2-vinyl-4,5-methylenedioxy)phenyl-2-benzyl-7,8-dimethoxy-1,2,3,4-tetrahydroisoquinoline and an unidentified material. The filtrate is neutralized, and the resulting free base is chromatographed on 10 g of alumina and eluated with 70 ml of benzene. The eluated material (0.85 g) is treated with 5 ml of ether, and the resulting crystals (0.32 g) are recrystallized from acetone to yield 296 mg of the cis-isomer of the aforementioned dibenzazecine as crystals having mp. 165°– 167°C. UV: $\lambda_{max}^{EtOH}$ 294 m$\mu$ ($\epsilon$ 6727). NMR: $\delta$(CDCl$_3$) 3.57 and 3.63 (2H each, singlet, N-CH$_2$-Ar), 3.73 and 3.77 (3H each, singlet, OCH$_3$), 5.73 (2H, singlet, O-CH$_2$-O). Anal. Calcd. for $C_{27}H_{27}NO_4$: C, 75.50%; H, 6.34%; N, 3.26%. Found: C, 75.64%; H, 6.41%; N, 3.36%.

The aforementioned trans-isomer (15.32 g) is dissolved in 300 ml of dioxane and shaken with 830 mg of platinum oxide is hydrogen atomosphere for 5 hours. After the catalyst is filtered off, the filtrate is evaporated to dryness under reduced pressure. The resulting crude base (17.4 g) is passed through a column of 87 g of silica gel and eluated with benzene to yield the pure base (15.58 g) which on recrystallization from an azeotropic mixture of benzene - n-hexane affords 15.64 g (93.2 %) of 6-benzyl-3,4-dimethoxy-10,11-methylenedioxy-5,6,7,8,13,14-hexahydrodibenz[c,g]azecine as colorless crystals having mp. 92° – 94°C. NMR: $\delta$(CDCl$_3$) 3.78 and 3.83 (3H each, singlet, OCH$_3$), 3.49 and 4.03 (2H each, singlet, N-CH$_2$-Ar), and 5.87 (2H, singlet, O-CH$_2$-O). Anal. Calcd. for $C_{27}H_{29}NO_4 \cdot 1/2 C_6H_6$ (benzene-adduct): C, 76.57%; H, 6.86%; N, 2.98%. Found: C, 76.28%; H, 6.92%, N, 2.85%.

In the same manner as mentioned above, the cis-isomer is also catalytically hydrogenated to yield the corresponding dibenz[c,g]azecine in 86 % yield.

EXAMPLE 2

To a solution of 124 g of 7-benzyl-9,10-dimethoxy-2,3-methylenedioxy-5,6,7,8,13,13a-hexaydrodibenzo[a,g]quinolizinium bromide in 1.35 liter of 99% methanol is added silver oxide prepared from 82.5 g of silver nitrate, and the suspension is stirred under heating at 53° – 55°C for 20 minutes. Insoluble part is removed by filtration and washed with 99% methanol. The washing is combined with the methanol filtrate and evaporated to dryness under reduced pressure to yield 116.3 g of the residue. To the residue is then added 485 ml of dimethylsulfoxide, and the mixture is vigorously stirred for 20 minutes. Ice-water (3 liter) is added thereto, and the mixture is extracted twice with benzene of one liter each. The benzene extract is washed with water, dried over anhydrous potassium carbonate, passed through a column of 500 g of alumina, eluated with benzene, and evaporated to dryness under reduced pressure. The resulting residue (93.7 g) is dissolved in a mixture of 10% hydrochloric acid (600 ml) and acetic acid (600 ml) and shaken in hydrogen atmosphere with 5 g of platinum oxide for 1 and 5/6 hours. The catalyst is filtered off, and the filtrate is concentrated in vacuo to about 800 ml volume, adjusted to pH 2.5 with 10% sodium hydroxide solution, then basified with sodium carbonate, and extracted with methylene chloride. The extract is washed with 5% sodium carbonate solution and then with water, dried over anhydrous sodium sulfate, and evaporated to dryness under reduced pressure to yield 83.5 g of the residue, which is chromatographed on 800 g of silica gel. Benzene and benzene-ethyl acetate elutions are combined and evaporated to dryness under reduced pressure, and the resulting crystalline residue is recrystallized from ether - n-hexane to yield 47.0 g (38.2 %) of 6-benzyl-3,4-dimethoxy-10,11-methylenedioxy-5,6,7,8,13,14-hexahydrodibenz[c,g]azecine as colorless prisms having mp. 75° – 78°C (as the ether adduct).

Under a similar manner as mentioned above, the following compounds can be produced.

3,4-Dimethoxy-11-hydroxy-6-methyl-5,6,7,8.13,14-hexahydrodibenz[c,g]azecine, mp. 135.5° – 137°C, the hydrochloride, mp. 236° – 238°C (dec), from 9,10-dimethoxy-2-hydroxy-7-methyl-5,6,7,8,13,13a-hexahydrodibenzo[a,g]quinolizinium bromide.

3,4-Dimethoxy-10-hydroxy-6-methyl-5,6,7,8,13,14-hexahydrodibenz[c,g]azecine, mp. 138° – 140°C, the hydrochloride, mp. 241.5° – 242.5°C (dec), from 9,10-dimethoxy-3-hydroxy-7-methyl-5,6,7,8,13,13a-hexahydrodibenzo[a,g]quinolizinium bromide.

6-Benzyl-3,4-dimethoxy-11-hydroxy-5,6,7,8,13,14-hexahydrodibenz[c,g]azecine, $\nu_{max}^{CHCl_3}$ 3603cm$^{-1}$, from 7-benzyl-9,10-dimethoxy-2-hydroxy-5,6,7,8,13,13a-hexahydrodibenzo[a,g]quinolizinium bromide.

6-Benzyl-3,4-dimethoxy-10-hydroxy-5,6,7,8,13,14-hexahydrodibenz[c,g]azecine, $\nu_{max}^{CHCl_3}$ 3603 and 3423 cm$^{-1}$, from 7-benzyl-9,10-dimethoxy-3-hydroxy-5,6,7,8,13,13a-hexahydrodibenzo[a,g]quinolizinium bromide.

6-Methyl-3,4,11-trimethoxy-5,6,7,8,13,14-hexahydrodibenz[c,g]azecine, mp. 89.5° – 91.5°C, from 7-methyl-2,9,10-trimethoxy-5,6,7,8,13,13a-hexahydrodibenzo[a,g]quinolizinium bromide.

6-Methyl-3,4,10-trimethoxy-5,6,7,8,13,14-hexahydrodibenz[c,g]azecine, mp. 121° – 122.5°C, from 7-methyl-3,9,10-trimethoxy-5,6,7,8,13,13a-hexahydrodibenzo[a,g]quinolizinium bromide.

10-hydroxymethyl-6-methyl-3,4,11-trimethoxy-5,6,7,8,13,14-hexahydrodibenz[c,g]azecine, mp. 133° – 135°C, from 3-hydroxymethyl-7-methyl-2,9,10-trimethoxy-5,6,7,8,13,13a-hexahydrodibenzo[a,g]quinolizinium bromide.

11-Methoxy-6-methyl-3,4-methylenedioxy-5,6,7,8,13,14-hexahydrodibenz[c,g]azecine, mp. 103.5°– 106.5°C, from 2-methoxy-7-methyl-9,10-methylenedioxy-5,6,7,8,13,13a-hexahydrodibenzo[a,g]quinolizinium bromide.

11-Hydroxymethyl-6-methyl-3,4,10-trimethoxy-5,6,7,8,13,14-hexahydrodibenz[c,g]azecine, mp. 135° – 137°C, from 2-hydroxymethyl-7-methyl-3,9,10-trimethoxy-5,6,7,8,13,13a-hexahydrodibenzo[a,g]quinolizinium bromide.

11-Hydroxy-6-methyl-3,4-methylenedioxy-5,6,7,8,13,14-hexahydrodibenz[c,g]azecine perchlorate, mp. 213°– 215°C, from 2-hydroxy-7-methyl-9,10-methylenedioxy-5,6,7,8,13,13a-hexahydrodibenzo[a,g]quinolizinium bromide.

3-Hydroxy-11-methoxy-6-methyl-5,6,7,8,13,14-hexahydrodibenz[c,g]azecine oxalate, mp. 199° – 202°C, from 10-hydroxy-2-methoxy-7-methyl-5,6,7,8,13,13a-hexahydrodibenzo[a,g]quinolizinium bromide.

3,11-Dimethoxy-6-methyl-5,6,7,8,13,14-hexahydrodibenz[c,g]azecine, mp. 74.5° – 76.5°C, from 2,10-dimethoxy-7-methyl-5,6,7,8,13,13a-hexahydrodibenzo[a,g]quinolizinium bromide.

4-Hydroxy-11-methoxy-6-methyl-5,6,7,8,13,14-hexahydrodibenz[c,g]azecine, mp. 106° – 108°C, from 9-hydroxy-2-methoxy-7-methyl-5,6,7,8,13,13a-hexahydrodibenzo[a,g]quinolizinium bromide.

3,11-Dihydroxy-6-methyl-5,6,7,8,13,14-hexahydrodibenz[c,g]azecine hydrobromide, mp. 259° –

260°C (dec), from 3,10-dihydroxy-7-methyl-5,6,7,8,13,13a-hexahydrodibenzo[a,g]quinolizinium bromide.

4,11-Dihydroxy-6-methyl-5,6,7,8,13,14-hexahydrodibenz[c,g]azecine perchlorate, mp. 217° – 219°C, from 2,9-dihydroxy-7-methyl-5,6,7,8,13,13a-hexahydrodibenzo[a,g]quinolizinium bromide.

6-Methyl-3,4,10-trihydroxy-5,6,7,8,13,14-hexahydrodibenz[c,g]azecine hydrobromide, mp. 121° – 123°C (dec), from 7-methyl-3,9,10-trihydroxy-5,6,7,8,13,13a-hexahydrodibenzo[a,g]quinolizinium bromide.

10-Hydroxy-6-methyl-3,4-methylenedioxy-5,6,7,8,13,14-hexahydrodibenz[c,g]azecine, mp. 151° – 152°C, from 3-hydroxy-7-methyl-9,10-methylenedioxy-5,6,7,8,13,13a-hexahydrodibenzo[a,g]quinolizinium bromide.

10-Methoxy-6-methyl-3,4-methylenedioxy-5,6,7,8,13,14-hexahydrodibenz[c,g]azecine, mp. 117° – 119°C, from 3-methoxy-7-methyl-9,10-methylenedioxy-5,6,7,8,13,13a-hexahydrodibenzo[a,g]quinolizinum bromide.

4-Hydroxy-10-methoxy-6-methyl-5,6,7,8,13,14-hexahydrodibenz[c,g]azecine perchlorate, mp. 211° – 213°C (dec), from 9-hydroxy-3-methoxy-7-methyl-5,6,7,8,13,13a-hexahydrodibenzo[a,g]quinolizinium bromide.

4,10-Dimethoxy-6-methyl-5,6,7,8,13,14-hexahydrodibenz[c,g]azecine, mp. 101.5° – 103°C, from 3,9-dimethoxy-7-methyl-5,6,7,8,13,13a-hexahydrodibenzo[a,g]quinolizinium bromide.

3,10-Dimethoxy-6-methyl-5,6,7,8,13,14-hexahydrodibenz[c,g]azecine, mp. 102° – 105°C, from 3,10-dimethoxy-7-methyl-5,6,7,8,13,13a-hexahydrodibenzo[a,g]quinolizinium bromide.

10-Hydroxy-6-methyl-5,6,7,8,13,14-hexahydrodibenz[c,g]azecine hydrochloride, mp. 271° – 272°C (dec), from 3-hydroxy-7-methyl-5,6,7,8,13,13a-hexahydrodibenzo[a,g]quinolizinium brimide.

3-Hydroxy-10-methoxy-6-methyl-5,6,7,8,13,14-hexahydrodibenz[c,g]azecine hydrochloride, mp. 233° – 235°C (dec), from 10-hydroxy-3-methoxy-7-methyl-5,6,7,8,13,13a-hexahydrodibenzo[a,g]quinolizinium bromide.

2,3-Dimethoxy-10-hydroxy-6-methyl-5,6,7,8,13,14-hexahydrodibenz[c,g]azecine hydrochloride, mp. 192° – 194°C (dec), from 10,11-dimethoxy-3-hydroxy-7-methyl-5,6,7,8,13,13a-hexanydrodibenzo[a,g]quinolizinium bromide.

10-Hydroxy-2-methoxy-6-methyl-5,6,7,8,13,14-hexahydrodibenz[c,g]azecine hydrochloride, mp. 247° – 249°C (dec), from 3-hydroxy-11-methoxy-7-methyl-5,6,7,8,13,13a-hexahydrodibenzo[a,g]quinolizinium bromide.

4,10-Dihydroxy-6-methyl-5,6,7,8,13,14-hexahydrodibenz[c,g]azecine perchlorate, mp. 195° – 197°C (dec), from 3,9-dihydroxy-6-methyl-5,6,7,8,13,13a-hexahydrodibenzo[a,g]quinolizinium bromide.

3,10-Dihydroxy-6-methyl-5,6,7,8,13,14-hexahydrodibenz[c,g]azecine hydrate, mp. 116° – 127°C, from 3,10-dihydroxy-7-methyl-5,6,7,8,13,13a-hexahydrodibenzo[a,g]quinolizinium bromide.

6-Methyl-3,4,10,11-tetrahydroxy-5,6,7,8,13,14-hexahydrodibenz[c,g]azecine hydrobromide, mp. 214° – 216°C, from 7-methyl-2,3,9,10-tetrahydroxy-5,6,7,8,13,13a-hexahydrodibenzo[a,g]quinolizinium bromide.

10,11-Dihydroxy-3,4-dimethoxy-6-methyl-5,6,7,8,13,14-hexahydrodibenz[c,g]azecine hydrochloride, mp. 236° – 238°C, from 2,3-dihydroxy-9,10-dimethoxy-7-methyl-5,6,7,8,13,13a-hexahydrodibenzo[a,g]quinolizinium bromide.

EXAMPLE 3

To a solution of 26 mg of 3,4-dimethoxy-6-benzyl-10-hydroxy-5,6,7,8,13,14-hexahydrodibenz[c,g]azecine in 1 ml of methanol is added 50 ml of 10% palladium-carbon and 0.2 ml of 6N-hydrochloric acid, and the mixture is shaken in hydrogen atmosphere at atmospheric pressure for 18 hours. The catalyst is removed by filtration, and the filtrate is evaporated to dryness under reuced pressure. Water is added to the residue, and the mixture is basified with 10% sodium bicarbonate solution and extracted with chloroform. The chloroform layer is washed with water, dried over anhydrous sodium sulfate, and evaporated to dryness to yield 17 mg of crystals, which on recrystallization from chloroform - methanol afford 3,4-dimethoxy-10-hydroxy-5,6,7,8,13,14-hexahydrodibenz[c,g]azecine as colorless prisms having mp. 205° – 206°C (dec). UV: $\nu_{max}^{EtOH}$ 281 m$\mu$ ($\epsilon$ 2740). IR: $\nu_{max}^{Nujol}$ 3305 cm$^{-1}$. Anal. Calcd. for $C_{19}H_{23}O_3N$: C, 72.82%; H, 7.40%, N 4.47%. Found: C, 73.03%; H, 7.15%; N, 4.32%.

In the similar manner as mentioned above, the following compounds can be produced.

3,4-Dimethoxy-11-hydroxy-5,6,7,8,13,14-hexahydrodibenz[c,g]azecine, mp. 223°– 224°C (dec), from 6-benzyl-3,4-dimethoxy-11-hydroxy-5,6,7,8,13,14-hexahydrodibenz[c,g]azecine.

3,4-Dimethoxy-10,11-methylenedioxy-5,6,7,8,13,14-hexahydrodibenz[c,g]azecine, mp. 143° – 143.5°C, from 6-benzyl-3,4-dimethoxy-10,11-methylenedioxy-5,6,7,8,13,14-hexahydrodibenz[c,g]azecine.

10,11-Dihydroxy-3,4-dimethoxy-5,6,7,8,13,14-hexahydrodibenz[c,g]azecine hydrochloride, mp. 126.5° – 128°C (dec), from 6-benzyl-10,11-dihydroxy-3,4-dimethoxy-5,6,7,8,13,14 hexahydrodibenz[c,g]azecine. 3,4,10,11,-Tetrahydroxy-5,6,7,8,13,14-hexahydrodibenz[c,g]azecine hydrochloride, mp. 127°–129°C (dec), from 6-benzyl-3,4,10,11-tetrahydroxy-5,6,7,8,13,14-hexahydrodibenz[c,g]azecine.

EXAMPLE 4

To a chromium trioxide - pyridine complex freshly prepared from 28 g of chromium trioxide and 280 ml of anhydrous pyridine is added dropwise a solution of 21 g of 10-benzyloxy-3,4-dimethoxy-6-methyl-5,6,7,8,13,14-hexahydrodibenz[c,g]azecine in 140 ml of pyridine at 10° – 15°C over a period of 35 minutes, and the mixture is allowed to stand at the same temperature for 2 hours and then at room temperature for 15 hours. The mixture is then diluted with 600 ml of ethyl acetate, stirred well, and filtered to remove the inorganic precipitate. The filtrate is passed through a column of alumina and celite (kiesel-guhr) and evaporated to dryness. The resulting residue (14.3 g) is dissolved in 286 ml of methanol, treated with 7 g of sodium borohydride, and chromatographed on 140 g of silica gel. The benzene - ethyl acetate (10 : 1) elution (2.45 g) is recrystallized from methylene chloride - ether to yield 2.11 g of 10-benzyloxy-3,4-dimethoxy-6-formyl-5,6,7,8,13,14-hexahydrodibenz[c,g]azecine as colorless needles having mp. 140° – 141°C. IR: $\nu_{max}^{CHCl_3}$ 1654 cm$^{-1}$. Anal. Calcd. for $C_{27}H_{29}O_4N$: C, 75.15%; H, 6.77%; N, 3.25%. Found: C, 75.20%; H, 7.02%; N, 3.23%.

This product (2.01 g) is dissolved in 50 ml of methanol and shaken with 2 g of 10% palladium-carbon in hydrogen atmosphere for 4 hours. The catalyst is removed by filtration, and the filtrate is evaporated to dryness under reduced pressure. The resulting residue (1.42 g) is recrystallized from methanol to yield 3,4-dimethoxy-6-formyl-10-hydroxy-5,6,7,8,13,14-hexahydrodibenz[c,g]azecine as prisms having mp. 226° – 228°C (dec). IR: $\nu_{max}^{CHCl_3}$ 3124 and 1654 cm$^{-1}$. Anal. Calcd. for $C_{20}H_{23}O_4N$: C, 70.36%; H, 6.79%; N, 4.10%. Found: C, 70.59%; H, 6.79%; N, 3.86%.

The said product (1.32 g) is dissolved in a mixed medium of 10% hydrochloric acid (132 ml) and n-propanol (43 ml), and the mixture is refluxed for 8 hours with stirring and then evaporated to dryness under reduced pressure. The resulting crystalline residue (1.25 g) is dissolved in hot water. The solution is filtered to remove insoluble material, basified with sodium carbonate, and then extracted with chloroform. The chloroform layer is washed with water, dried over anhydrous sodium sulfate, and evaporated to dryness under reduced pressure to yield 1.02 g of the crystalline residue, which on recystallization from chloroform - methanol affords 840 mg of 3,4-dimethoxy-10-hydroxy-5,6,7,8,13,14-hexahydrodibenz[c,g]azecine as colorless prisms having mp. 205° – 206°C (dec). IR: $\nu_{max}^{Nujol}$ 3305 cm$^{-1}$. Anal. Calcd. for $C_{19}H_{23}O_3N$: C, 72.82%; H, 7.40%; N, 4.47%. Found: C, 73.03%; H, 7.15%; N, 4.32%.

EXAMPLE 5

Platinum oxide (50 mg) is hydrogenated in 50 ml of ethanol by shaking in hydrogen atmosphere. To this catalyst is added a solution of 51mg of 3,4-dimethoxy-10-hydroxy-5,6,7,8,13,14-hexahydrodibenz[c,g]azecine and 1 ml of 37% formaldehyde in 5 ml of ethanol, and the mixture is shaken in hydrogen atmosphere for 6 hours. After removal of the catalyst by filtration, the mixture is evaporated to dryness under reduced pressure, and the residue (46 mg) is chromatographed on thin layer plates of silica gel containing 0.2N-sodium hydroxide [developed by chloroform - methanol (20 : 1)]. The product is recrystallized from benzene to yield 35 mg of 3,4-dimethoxy-10-hydroxy-6-methyl-5,6,7,8,13,14-hexahydrodibenz[c,g]azecine as colorless crystals having mp. 138° – 140°C. IR: $\nu_{max}^{Nujol}$ 3461 cm$^{-1}$.

The hydrochloride, mp. 241.5° – 242.5°C (dec) (recrystallized from water). The hydrobromide, mp. 236° – 239°C (recrystallized from water).

In the same manner as mentioned above, the following compounds can be produced.

3,4-Dimethoxy-11-hydroxy-6-methyl-5,6,7,8,13,14-hexahydrodibenz[c,g]azecine, mp. 135.5 - 137°C, from 3,4-dimethoxy-11-hydroxy-5,6,7,8,13,14-hexahydrodibenz[c,g]azecine and formaldehyde.

6-Benzyl-3,4-dimethoxy-10-hydroxy-5,6,7,8,13,14-hexahydrodibenz[c,g]azecine, $\nu_{max}^{CHCl_3}$ 3603 and 3423 cm$^{-1}$, from 3,4-dimethoxy-10-hydroxy-5,6,7,8,13,14-hexahydrodibenz[c,g]azecine and benzaldehyde.

6-Bnezyl-3,4-dimethoxy-11-hydroxy-5,6,7,8,13,14-hexahydrodibenz[c,g]azecine, $\nu_{max}^{CHCl_3}$ 3603 cm$^{-1}$, from 3,4-dimethoxy-11-hydroxy-5,6,7,8,13,14-hexahydrodibenz[c,g]azecine and benzaldehyde.

3,4-Dimethoxy-10-hydroxy-6-isobutyl-5,6,7,8,13,14-hexahydrodibenz[c,g]azecine hydrochloride, mp. 214° – 215°C (dec), from 3,4-dimethoxy-10-hydroxy-5,6,7,8,13,14-hexahydrodibenz[c,g]azecine and isobutyraldehyde.

3,4-Dimethoxy-11-hydroxy-6-isobutyl-5,6,7,8,13,14-hexahydrodibenz[c,g]azecin hydrochloride, mp. 218° – 219°C (dec), from 3,4-dimethoxy-11-hydroxy-5,6,7,8,13,14-hexahydrodibenz[c,g]azecine and isobutyraldehyde.

EXAMPLE 6

A mixture of 100 mg of 3,4-dimethoxy-10-hydroxy-5,6,7,8,13,14-hexahydrodibenz[c,g]azecine, 42.6 ml of allyl bromide and 32.3 mg of sodium bicarbonate in 4 ml of dimethylformaide is stirred for 2 hours at 100°C in argon atmosphere. After cooling, 40 ml of water is added to the mixture, and the mixture is extracted with methylene chloride. The extract is washed with water, dried over anhydrous sodium sulfate, and evaporated to dryness under reduced pressure. The residue is dissolved in benzene, passed through a column of 3.8 g of silica gel, and eluated with benzene - ethyl acetate (10 : 1). The evaporation of the solvent affords 106 mg of 6-allyl-3,4-dimethoxy-10-hydroxy-5,6,7,8,13,14-hexahydrodibenz[c,g]azecine as a colorless oily material. IR: $\nu_{max}^{CHCl_3}$ 3604, 3420 and 1641 cm$^{-1}$.

The hydrochloride, as colorless prisms recrystallized from ethanol - acetone, mp. 219° – 220°C (dec). Anal. Calcd. for $C_{22}H_{27}O_3N \cdot HCl$: C, 67.77%; H, 7.24%; N, 3.59%; Cl, 9.09%. Found: C, 67.89%; H, 7.29%; N, 3.41%; Cl, 9.28%.

In the similar manner as described above, the following compounds can be produced.

6-Allyl-3,4-dimethoxy-11-hydroxy-5,6,7,8,13,14-hexahydrodibenz[c,g]azecine hydrochloride, mp. 231° – 232°C (dec), from 3,4-dimethoxy-11-hydroxy-5,6,7,8,13,14-hexahydrodibenz[c,g]azecine and allyl bromide.

6-Benzyl-3,4-dimethoxy-10-hydroxy-5,6,7,8,13,14-hexahydrodibenz[c,g]azecine hydrochloride, mp. 185° – 186°C (dec), from 3,4-dimethoxy-10-hydroxy-5,6,7,8,13,14-hexahydrodibenz[c,g]azecine and benzyl chloride.

6-Benzyl-3,4-dimethoxy-11-hydroxy-5,6,7,8,13,14-hexahydrodibenz[c,g]azecine hydrochloride, mp. 244° – 245°C (dec), from 3,4-dimethoxy-11-hydroxy-5,6,7,8,13,14-hexahydrodibenz[c,g]azecine and benzyl chloride.

3,4-Dimethoxy-10-hydroxy-6-(3-methyl-2-butenyl)-5,6,7,8,13,14-hexahydrodibenz[c,g]azecine hydrochloride, mp. 210° – 211°C (dec), from 3,4-dimethoxy-10-hydroxy-5,6,7,8,13,14-hexahydrodibenz[c,g]azecine and 3-methyl-2-butenyl bromide.

3,4-Dimethoxy-11-hydroxy-6-(3-methyl-2-butenyl)-5,6,7,8,13,14-hexahydrodibenz[c,g]azecine hydrochloride, mp. 231° – 232°C (dec), from 3,4-dimethoxy-11-hydroxy-5,6,7,8,13,14-hexahydrodibenz[c,g]azecine and 3-methyl-2-butenyl bromide.

3,4-Dimethoxy-10-hydroxy-6-phenethyl-5,6,7,8,13,14-hexahydrodibenz[c,g]azecine, $\nu_{max}^{CHCl_3}$ 3603 and 3420 cm$^{-1}$, from 3,4-dimethoxy-10-hydroxy-5,6,7,8,13,14-hexahydrodibenz[c,g]azecine and phenethyl iodide.

6-Cyclopropylmethyl-3,4-dimethoxy-10-hydroxy-5,6,7,8,13,14-hexahydrodibenz[c,g]azecine hydrochloride, mp. 229° – 230°C (dec), from 3,4-dimethoxy- 10-hydroxy-5,6,7,8,13,14-hexahydrodibenz[c,g]azecine and cyclopropylmethyl bromide.

6-Cyclopropylmethyl-3,4-dimethoxy-11-hydroxy-5,6,7,8,13,14-hexahydrofibenz[c,g]azecine hydrochloride, mp. 238° - 239°C (dec), from 3,4-dimethoxy-11-hydroxy-5,6,7,8,13,14-hexahydrodibenz[c,g]azecine and cyclopropylmethyl bromide.

EXAMPLE 7

To 29 ml of liquid ammonia dried with a small quantity of potassium under cooling at −60 ~−65°C are added 963 mg of 9,10-dimethoxy-7-methyl-2,3-methylenedioxy-5,6,7,8,13,13a-hexahydrodibenzo[a,g]quinolizinium iodide (N-methyl-tetrahydroberberinium iodide), 10 ml of anhydrous tetrahydrofuran and 148 mg of anhydrous tert-butanol with stirring, and then 610 mg of potassium in small portions, and the mixture is stirred at −60 ~−65°C for 2.5 hours. Then, ammonium chloride is added to the mixture, and ammonia is distilled off. To the residue is added water, and then extracted with benzene. The benzene layer is washed with water, evaporated to dryness, chromatographed on silica gel thin layer plates, and developed with chloroform - methanol (97 : 3) to yield 180 mg of 3,4-dimethoxy-10-hydroxy-6-methyl-5,6,7,8,13,14-hexahydrodibenz[c,g]azecine as crystals having mp. 138° - 140°C, and 200 mg of 3,4-dimethoxy-11-hydroxy-6-methyl-5,6,7,8,13,14-hexahydrodibenz[5,6,7,8,13,14]azecine as colorless crystals having mp. 135.5° - 137°C.

EXAMPLE 8

To 45 ml of liquid ammonia dried with a small quantity of metal lithium under cooling at −65 ~−70°C are added 1.3 g of 7-allyl-9,10-dimethoxy-2,3-methylenedioxy-5,6,7,8,13,14-hexahydrodibenzo[a,g]quinolizinium bromide (i.e. N-allyltetrahydroberberinium bromide) and 14 ml of anhydrous tetrahydrofuran, and then 159 mg of lithium in small portions, and the mixture is stirred at −65 ~−70°C for 2 hours. Ammonium chloride is added to the reaction mixture, and ammonia is distilled off. To the residue is added water and extracted with benzene. The benzene layer is washed with water, evaporated to dryness, and chromatographed on silica gel thin layer plates to yield 6-allyl-3,4-dimethoxy-10-hydroxy-5,6,7,8,13,14-hexahydrodibenz[c,g]azecine as an oily meterial and 6-allyl-3,4-dimethoxy-11-hydroxy-5,6,7,8,13,14-hexahydrodibenz[c,g]azecine as another oily material.

The 10-hydroxy derivative: IR: $\nu_{max}^{CHCl_3}$ 3604, 3420 and 1641 cm$^{-1}$. UV: $\lambda_{max}^{95\%EtOH}$ 281 m$\mu$($\epsilon$3620).

The 11-hydroxy derivative: IR: $\nu_{max}^{CHCl_3}$ 3606 and 3420 cm$^{-1}$.

In the same manner as described above, the following compounds can be produced.

6-Benzyl-3,4-dimethoxy-10-hydroxy-5,6,7,8,13,14-hexahydrodibenz[c,g]azecine (the hydrochloride, mp. 185° - 186°C (dec)) and 6-benzyl-3,4-dimethoxy-11-hydroxy-5,6,7,8,13,14-hexahydrodibenz[c,g]azecine (the hydrochloride, mp. 244° - 245°C (dec)) from 7-benzyl-9,10-dimethoxy-2,3-methylenedioxy-5,6,7,8,13,13a-hexahydrodibenzo[a,g]quinolizinium bromide.

6-Cyclopropylmethyl-3,4-dimethoxy-10-hydroxy-5,6,7,8,13,14-hexahydrodibenz[c,g]azecine (the hydrochloride, mp. 229 - 230°C (dec)) and 6-cyclopropylmethyl-3,4-dimethoxy-11-hydroxy-5,6,7,8,13,14-hexahydrodibenz[c,g]azecine (the hydrochloride, mp. 238 - 239°C (dec)) from 7-cyclopropylmethyl-9,10-dimethoxy-2,3-methylenedioxy-5,6,7,8,13,13a-hexahydrodibenzo[a,g]quinolizinium bromide.

3,4-Dimethoxy-10-hydroxy-6-isobutyl-5,6,7,8,13,14-hexahydrodibenz[c,g]azecine (the hydrochloride, mp. 214° - 215°C (dec)) and 3,4-dimethoxy-11-hydroxy-6-isobutyl-5,6,7,8,13,14-hexahydrodibenz[c,g]azecine (the hydrochloride, mp. 218° - 219°C (dec)) from 9,10-dimethoxy-7-isobutyl-2,3-methylenedioxy-5,6,7,8,13,13a-hexahydrodibenzo[a,g]quinolizinium bromide.

EXAMPLE 9

To 4 liters of liquid ammonia dried with a small quantity of metal lithium under cooling at −60 ~−65°C is added dropwise a solution of 95.9 g of 3,4-dimethoxy-6-methyl-10,11-methylenedioxy-5,6,7,8,13,14-hexahydrodibenz[c,g]azecine in 575 ml of anhydrous tetrahydrofuran, and then 7.89 g of lithium in small portions within a period of 3 hours while stirring the mixture. Then 70 g of ammonium chloride is added to the mixture, and ammonia is distilled off. To the residue is added water, and extracted with benzene. The benzene layer is washed with water and evaporated to dryness under reduced pressure, and the residue is separated by means of thin layer chromatography using silica gel to yield 3,4-dimethoxy-10-hydroxy-6-methyl-5,6,7,8,13,14-hexahydrodibenz[c,g]azecine as colorless crystals having mp. 138° - 140°C, 3,4-dimethoxy-11-hydroxy-6-methyl-5,6,7,8,13,14-hexahydrodibenz[c,g]azecine as crystals having mp. 135.5° - 137°C, 3,4-dimethoxy-10-hydroxy-11-hydroxymethyl-6-methyl-5,6,7,8,13,14-hexahydrodibenz[c,g]-azecine as crystals having mp. 164° - 165°C (dec), and 3,4-dimethoxy-11-hydroxy-10-hydroxymethyl-6-methyl-5,6,7,8,13,14-hexahydrodibenz[c,g]azecin as colorless crystals having mp. 193° - 193.5°C (dec).

We claim:
1. A compound of the formula:

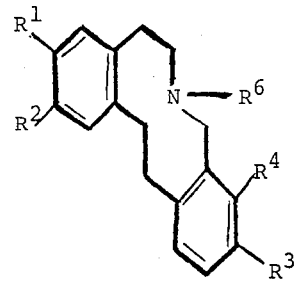

wherein $R^1$ and $R^2$ are each selected from the group consisting of hydrogen, hydroxy and hydroxymethyl; one of $R^3$ and $R^4$ is selected from the group consisting of hydrogen, hydroxy and methoxy and the other is selected from the group consisting of hydroxy and methoxy and $R^6$ is selected from the group consisting of hydrogen, methyl, cyclopropylmethyl and benzyl.

2. A compound claimed in claim 1, namely 3,4-dimethoxy-11-hydroxy-6-methyl-5,6,7,8,13,14-hexahydrodibenz[c,g]azecine and acid addition salts thereof.

3. A compound claimed in claim 1, namely 3,4-dimethoxy-10-hydroxy-6-methyl-5,6,7,8,13,14-hexahydrodibenz[c,g]azecine and acid addition salts thereof.

4. A compound claimed in claim 1, namely 3,4-dimethoxy-11-hydroxy-10-hydroxymethyl-6-methyl-5,6,7,8,13,14-hexahydrodibenz[c,g]azecine and acid addition salts thereof.

5. A compound claimed in claim 1, namely 3,4-dimethoxy-10-hydroxy-11-hydroxymethyl-6-methyl-5,6,7,8,13,14-hexahydrodibenz[c,g]azecine and acid addition salts thereof.

6. A compound claimed in claim 1, namely 10,11-dihydroxy-3,4-dimethoxy-5,6,7,8,13,14-hexahydrodibenz[c,g]azecine and acid addition salts thereof.

7. A compound claimed in claim 1, namely 3,4-dimethoxy-10-hydroxy-5,6,7,8,13,14-hexahydrodibenz[c,g]azecine and acid addition salts thereof.

8. A compound claimed in claim 1, namely 6-cyclopropylmethyl-3,4-dimethoxy-10-hydroxy-5,6,7,8,13,14-hexahydrodibenz[c,g]azecine and acid addition salts thereof.

* * * * *